US012109394B2

(12) United States Patent
Chin et al.

(10) Patent No.: US 12,109,394 B2
(45) Date of Patent: Oct. 8, 2024

(54) SYRINGE FOR DERMAL REGENERATION

(71) Applicants: Se Hoon Chin, Gyeonggi-do (KR); Joong Suk Jin, Gyeonggi-do (KR)

(72) Inventors: Se Hoon Chin, Gyeonggi-do (KR); Joong Suk Jin, Gyeonggi-do (KR)

( * ) Notice: Subject to any disclaimer, the term of this patent is extended or adjusted under 35 U.S.C. 154(b) by 904 days.

(21) Appl. No.: 17/269,829

(22) PCT Filed: Jun. 28, 2019

(86) PCT No.: PCT/KR2019/007886
§ 371 (c)(1),
(2) Date: Feb. 19, 2021

(87) PCT Pub. No.: WO2020/067631
PCT Pub. Date: Apr. 2, 2020

(65) Prior Publication Data
US 2021/0316073 A1 Oct. 14, 2021

(30) Foreign Application Priority Data
Sep. 27, 2018 (KR) .................. 10-2018-0114978

(51) Int. Cl.
A61M 5/178 (2006.01)
A61M 5/315 (2006.01)
(Continued)

(52) U.S. Cl.
CPC .......... *A61M 5/1782* (2013.01); *A61M 5/315* (2013.01); *A61M 5/3286* (2013.01);
(Continued)

(58) Field of Classification Search
None
See application file for complete search history.

(56) References Cited

U.S. PATENT DOCUMENTS

| 2011/0238038 A1* | 9/2011 | Sefi ................. A61M 5/46 604/117 |
| 2012/0191036 A1 | 7/2012 | Chin et al. |
| 2017/0056594 A1* | 3/2017 | Chin ................. A61M 5/3129 |

FOREIGN PATENT DOCUMENTS

| CN | 102762245 A | 10/2012 |
| CN | 105939741 A | 9/2016 |

(Continued)

OTHER PUBLICATIONS

Korean Office Action dated Jul. 1, 2020 in corresponding Korean Application No. 10-2018-0114978.
(Continued)

*Primary Examiner* — Manuel A Mendez
(74) *Attorney, Agent, or Firm* — Fox Rothschild LLP

(57) ABSTRACT

Proposed is a syringe for dermis regeneration, the syringe including: an injection unit having a first space therein and being open at a rear end portion, the first space being filled with a liquid or a gas and communicating with the outside; a needle combined with a front end portion of the injection unit and having a space therein, the space communicating with the first space; a liquid supply unit having a first end portion removably combined with the rear end portion, having a second end portion through which a piston moves, and having a space therein, the space being filled with the liquid and communicating with the first space, and the piston being inserted into the liquid supply unit; and a gas injection port passing through a sidewall of the injection unit and communicating with the first space to allow the first space to be filled with the gas.

13 Claims, 7 Drawing Sheets

(51) Int. Cl.
    *A61M 5/32* (2006.01)
    *A61M 5/00* (2006.01)
    *A61M 5/31* (2006.01)

(52) U.S. Cl.
    CPC .......... *A61M 2005/006* (2013.01); *A61M 2005/1787* (2013.01); *A61M 2005/3128* (2013.01)

(56) References Cited

FOREIGN PATENT DOCUMENTS

| | | | |
|---|---|---|---|
| CN | 106727244 A | 5/2017 |
| JP | 2009090098 A | 4/2009 |
| JP | 2017504462 A | 2/2017 |
| KR | 10-2012-0103661 A | 9/2012 |
| KR | 10-1180113 B1 | 9/2012 |
| KR | 10-1236403 B1 | 2/2013 |
| KR | 144-0838 | 9/2014 |
| KR | 10-1491576 B1 | 2/2015 |
| KR | 10-1685660 B1 | 12/2016 |
| KR | 10-1879211 B1 | 7/2018 |
| WO | 2011/090699 A2 | 7/2011 |

OTHER PUBLICATIONS

Korean Office Action issued Dec. 30, 2019 in coresponding Korean Application No. 10-2018-0114978.
Korean Office Action issued Dec. 22, 2020 in corresponding Korean Application No. 10-2018-0114978.

* cited by examiner

[Fig.1]
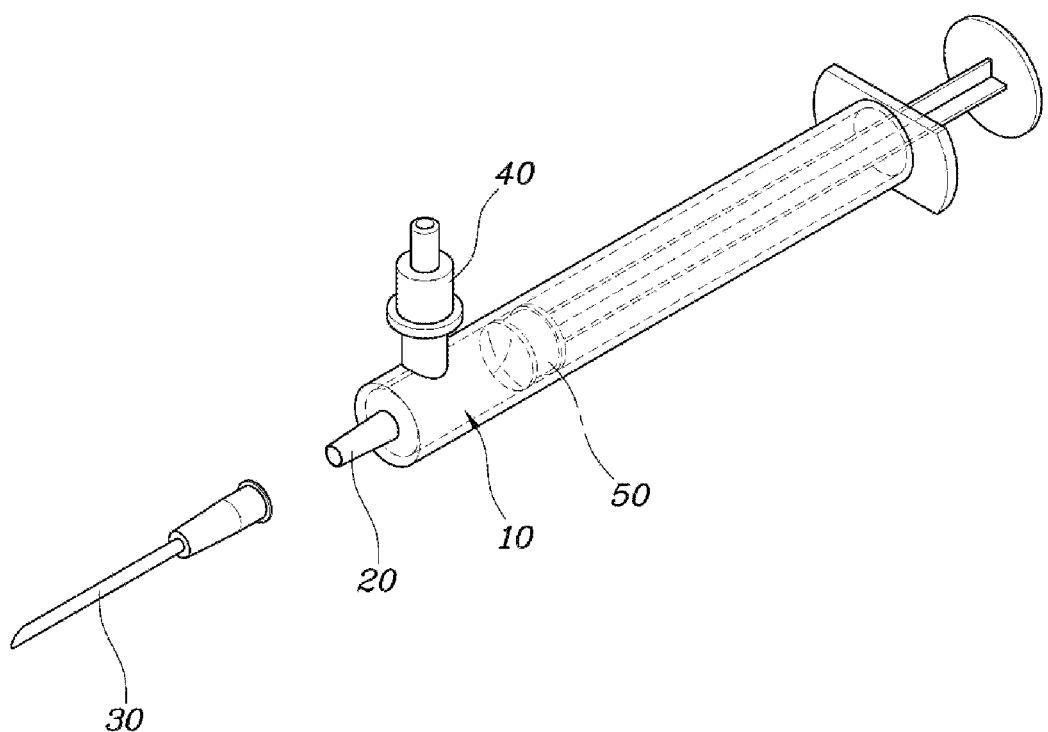

[Fig. 2]
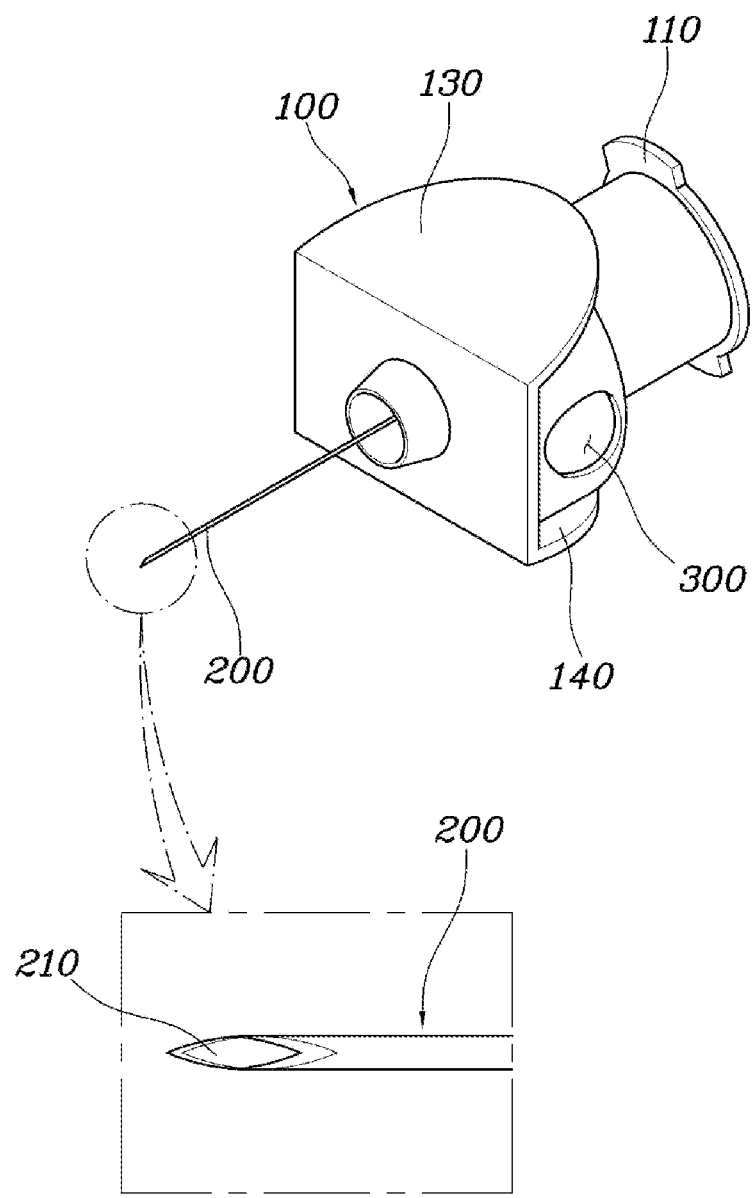

[Fig. 3]
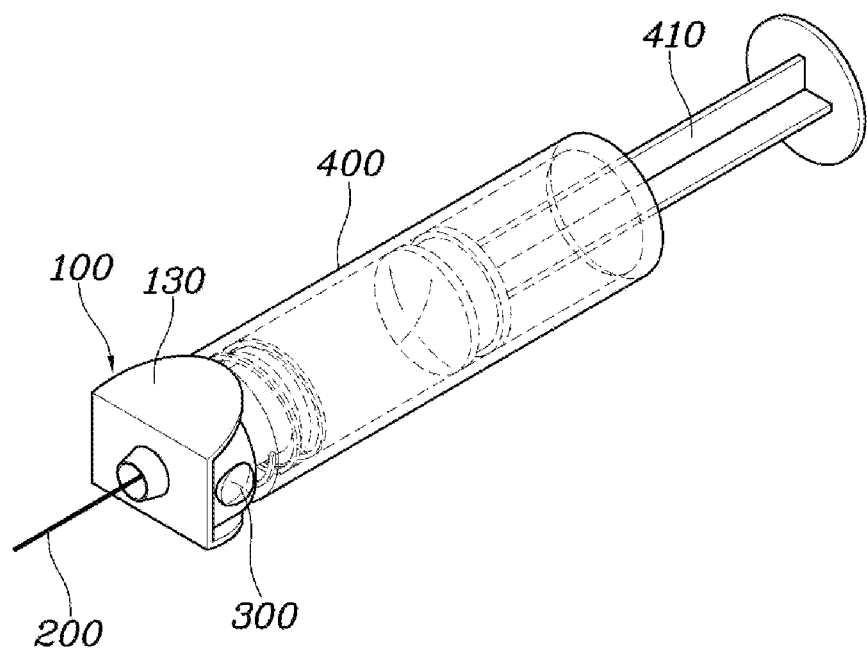

[Fig. 4]
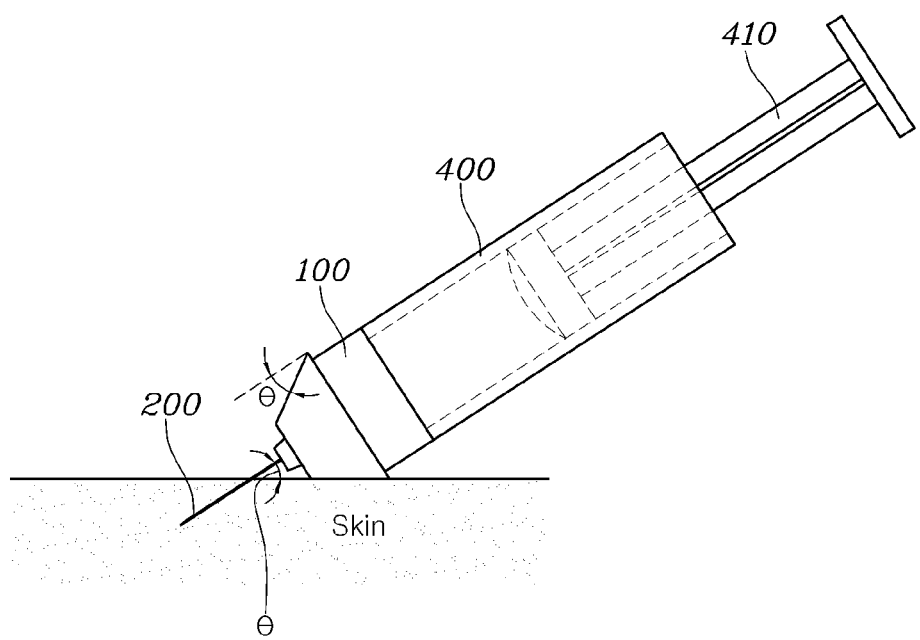

[Fig. 5]
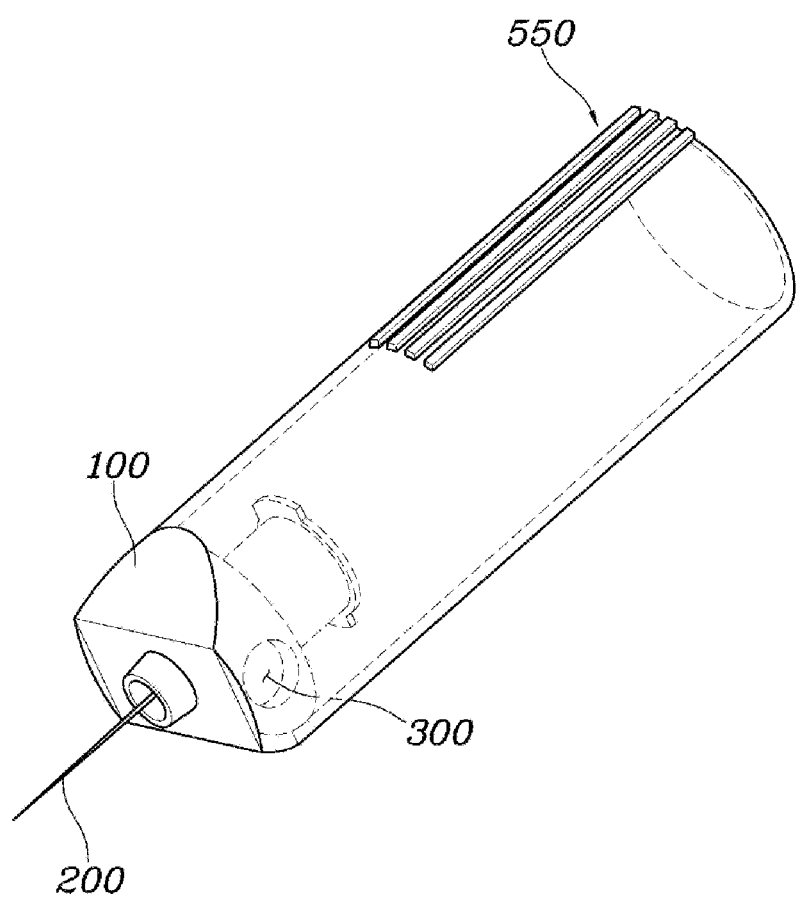

[Fig. 6]
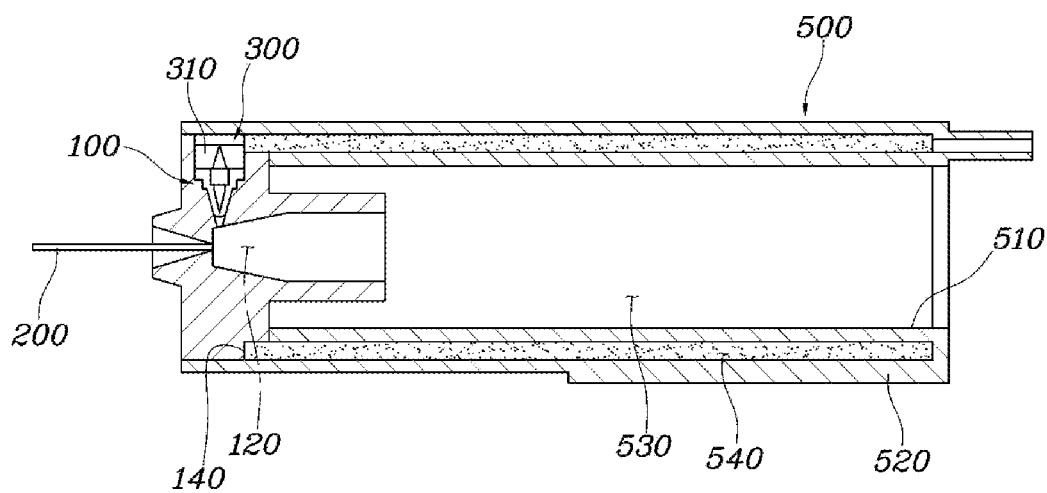

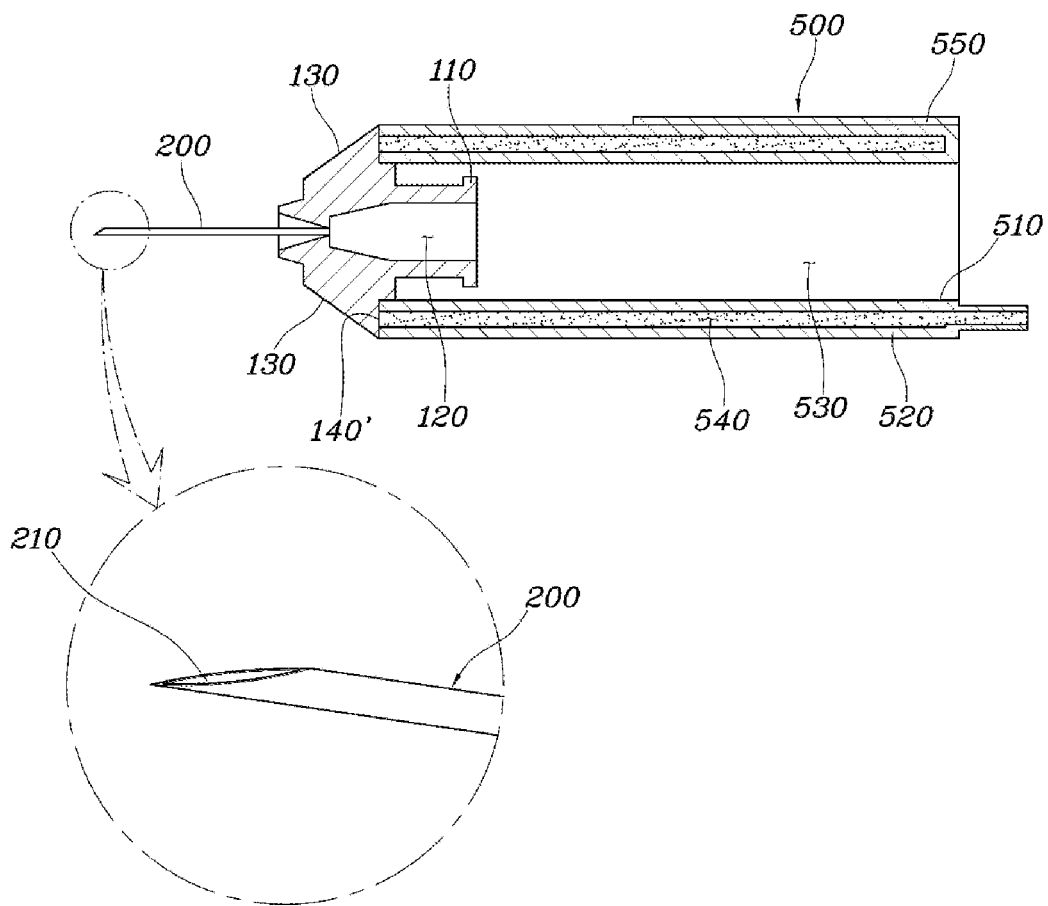
[Fig. 7]

SYRINGE FOR DERMAL REGENERATION

CROSS-REFERENCE TO RELATED APPLICATIONS

This application is a National Phase application filed under 35 USC 371 of PCT International Application PCT/KR2019/007886 with an International Filing Date of Jun. 28, 2019 which claims priority from Korean Application 10-2018-0114978 filed on Sep. 27, 2018. The entire contents of these applications are incorporated herein by reference in their entirety.

TECHNICAL FIELD

The present invention relates to a syringe for dermis regeneration, which is capable of selectively injecting a gas such as carbon dioxide and a drug solution such as hyaluronic acid and thus enabling dermis, which is an inner layer of skin, to be easily regenerated.

BACKGROUND ART

In the case of a retracted scar and a deep wrinkle that have been difficult to cure, a minute amount of gas, determined by a doctor, is first injected into a dermis layer to split the dermis layer and a precisely determined minute amount of liquid is injected into the split dermis layer to cause physical, chemical, and biological stimuli at the same time. Thus, a cure for the retracted scar and the deep wrinkle is possible by generating a large amount of collagen fibrous tissue at a determined point.

Therefore, in order for the doctor to achieve dermis self-regeneration, there is a need to alternately inject a gas and a liquid in a state where a needle of one syringe remains in a patient's skin. To this end, a syringe with a special structure is required.

FIG. 1 is a view illustrating a syringe in the related art.

With reference to FIG. 1, in a syringe in the related art, a guidance pipe 20 protruding to the outside to be combined with a needle 30 is provided on a discharge unit 10 from which an internal liquid is discharged. In this case, a considerable amount of fluid remains in the guidance pipe 20.

However, in a syringe for dermis regeneration, in a state where the needle 30 remains in the skin, a piston 50 moves backward, thereby introducing a gas into the discharge unit 10 through a gas inlet port 40, and the piston 50 moves forward, thereby introducing the gas through the guidance pipe 20. Subsequently, a liquid is injected. In this manner, the gas and the liquid have to be alternately injected.

However, when the gas introduced into the discharge unit 10 is injected, there occurs a problem in that the liquid remaining in the guidance pipe 20 is injected earlier than the gas. Therefore, the injection of the liquid and the gas cannot be precisely controlled.

The foregoing is intended merely to aid in understanding the background of the present invention and therefore should not be interpreted to admit that the present invention falls within the purview of the related art that is already known to a person of ordinary skill in the art.

Examples of the related art may be referred to Korean Patent No. 10-1440838 B1.

DISCLOSURE

Technical Problem

An objective of the present invention, which was devised to solve the above-described problem, is to provide a syringe for dermis regeneration, which is capable of preventing a liquid from remaining within a needle of an injection unit when injecting a gas into the injection unit and thus preventing the liquid from being injected earlier than the gas when injecting the gas through the needle.

Technical Solution

According to an aspect of the present invention, there is provided a syringe for dermis regeneration, the syringe including: an injection unit having a first space therein and being open at a rear end portion thereof, the first space being filled with a liquid or a gas and communicating with the outside through the open rear end portion; a needle combined with a front end portion of the injection unit and having a space therein, the space of the needle communicating with the first space; a liquid supply unit having a first end portion removably combined with the rear end portion of the injection unit, having a second end portion through which a piston moves backward or forward, and having a space therein, the space of the liquid supply unit being filled with the liquid and communicating with the first space, and the piston being inserted into the liquid supply unit through the second end portion of the liquid supply unit; and a gas injection port passing through a sidewall of the injection unit and communicating with the first space to allow the first space to be filled with the gas introduced through the gas injection port.

In the syringe, the gas injection port may pass through the sidewall of the injection unit in a manner that is adjacent to a rear end portion of a needle positioned in front of the first space and may communicate with the first space.

In the syringe, in a state where the liquid supply unit is combined with the injection unit, when the piston moves forward, the liquid within the liquid supply unit may be discharged into the needle through the first space, and when the piston moves backward, a negative pressure may be formed in the first space, and thus the gas may be introduced into the first space through the gas injection port.

In the syringe, a check valve may be provided in the gas injection port, and the gas may be injected into the first space through the gas injection port, but the liquid or the gas within the first space may not flow to the outside through the gas injection port.

In the syringe, the injection unit may have an inclination surface on a portion of the sidewall, the portion being positioned at a location that does not overlap the gas injection port, and the inclination portion being inclined toward a centerline of the injection unit in a forward direction.

In the syringe, the inclination surface of the injection unit may have inclination surfaces formed on opposite sides of the sidewall, the inclination surfaces having a form of facing each other.

In the syringe, the gas injection port may be positioned on the sidewall of the injection unit at a location between the opposite inclination surfaces facing each other.

In the syringe, the injection unit may be cylinder-shaped and may have inclination surfaces formed by cutting opposite sides of a front surface of the injection unit in outward directions.

In the syringe, the needle may have a cut surface that is formed by obliquely cutting a front end portion of the needle in one direction.

In the syringe, the needle may have a cut surface that is formed by obliquely cutting a front end portion of the needle in a direction parallel with the inclination surface of the injection unit.

The syringe may further include: a cylinder having a double-tube structure that includes an inner tube and an outer tube that are connected to a rear end portion of the injection unit, the inner tube having a second space therein and a third space being formed between the inner tube and the outer tube, wherein the liquid supply unit communicating with the first space may be positioned within the second space, and the third space may communicate with the first space through the gas injection port and may be filled with the gas.

In the syringe, a sidewall of the injection unit may have a combination end portion recessed inward and the cylinder may be combined with the combination end portion in such a manner that the second space is sealed by the combination end portion.

In the syringe, the injection unit may have inclination surfaces on portions of a sidewall thereof, the portions being positioned at locations that do not overlap the gas injection port, and the inclination portions being inclined toward a centerline of the injection unit in a forward direction, and the outer tube of the cylinder in a direction adjacent to the inclination surfaces of the injection unit may have a guidance portion on a sidewall thereof, the guidance portion including a plurality of grooves and a plurality of protrusions that are positioned in an alternating manner.

According to another aspect of the present invention, there is provided a syringe for dermis regeneration, the syringe including: an injection unit having a first space therein and being open at a rear end portion thereof, the first space being filled with a liquid or a gas and communicating with the outside through the pen rear end portion; a cylinder having a double-tube structure that comprises an inner tube and an outer tube that are integrally combined with a rear end portion of the injection unit, the inner tube having a second space therein and a third space being formed between the inner tube and the outer tube; a needle combined with a front end portion of the injection unit and having a space therein, the space of the needle communicating with the first space; a liquid supply unit having a first end portion removably combined with the rear end portion of the injection unit, having a second end portion through which a piston moves backward or forward, and having a space therein, the space of the liquid supply unit being filled with the liquid and communicating with the first space, and the piston being inserted into the liquid supply unit through the second end portion of the liquid supply unit; and a gas injection port passing through a sidewall of the injection unit and communicating with the first space and the third space, the first space being filled with the gas introduced from the third space through the gas injection port.

Advantageous Effects

With the syringe for dermis regeneration according to the present invention, when a gas is supplied through a gas inlet port and then the gas is injected through a needle, a remaining liquid can be prevented from being earlier injected than the gas.

In addition, an inclination surface of an injection unit is positioned in a different direction than a check valve. Thus, even a needle with a relatively short length can easily enter skin in an oblique manner.

In addition, the needle has a cut surface that is formed by obliquely cutting an injection port of the needle. Thus, a drug solution can be injected upward in a state where the needle remains in the skin. Therefore, the effect obtained by injecting the drug solution can be increased.

DESCRIPTION OF DRAWINGS

FIG. 1 is a view illustrating a syringe in the related art;

FIG. 2 is a perspective view illustrating an injection unit of a syringe for dermis regeneration according to an embodiment of the present invention;

FIG. 3 is a perspective view illustrating the syringe for dermis regeneration according to the embodiment of the present invention;

FIG. 4 is a view illustrating a state where a needle of the syringe for dermis regeneration according to the embodiment of the present invention enters skin;

FIG. 5 is a view illustrating a syringe for dermis regeneration according to another embodiment of the present invention; and FIGS. 6 and 7 are cross-sectional views each illustrating a syringe for dermis regeneration according to still another embodiment of the present invention.

MODE FOR INVENTION

Embodiments of the present invention, which are disclosed in the present specification or application, will be described for illustrative purpose in terms of specific structures and functions. The embodiments of the present invention can be implemented in various ways, and the present invention should not be construed as being limited to the embodiments that are described in the present specification or application.

Various modifications may be made in various ways to the embodiments of the present invention. The embodiments of the present invention may have various forms. Therefore, exemplary embodiments will be described in detail in the present specification or application with reference to the accompanying drawings. However, this description is not intended to limit the technical idea of the present invention to the specifically disclosed embodiments. All alterations, equivalents, and substitutes that are included within the technical idea of the present invention should be understood as falling within the scope of the present invention.

The terms first, second, and so on are used to describe various constituent elements but should not be construed as imposing any limitation on the various constituent elements. Those terms are only used to distinguish one constituent element from another. For instance, a first constituent element may be termed a second constituent element without departing from the scope of each claim that defines the present invention. Likewise, the second constituent element may also be termed the first constituent element.

It should be understood that, when a constituent element is referred to as being "coupled to" or "connected to" a different constituent element, this means that the constituent element may be directly coupled to or directly connected to the different constituent element or means that an intervening constituent element may be present therebetween. In contrast, it should be understood that, when a constituent element is referred to as being "directly coupled to" or "directly connected to" a different constituent element, this means that no intervening constituent element is present therebetween. This is true for expressions describing a relationship between constituent elements. For example, expressions, such as "between" and "directly between", and expressions, such as "adjacent to" and "directly adjacent to", should also be construed in the same manner.

The terms in the present specification are used only for describing exemplary embodiments and are not intended to limit the present invention. The indefinite article "a/an" is used to mean "one or more", not only one, except as distinctively expressed in context. It should be understood that, throughout the present specification, the terms "include", "have", or the like are intended to indicate that a feature, a number, a step, an operation, a constituent element, a component, or any combination thereof is present, without precluding the presence or addition of one or more other features, numbers, steps, operations, constituent elements, or any combination thereof.

Unless otherwise defined, each of the technical or scientific terms used through the present specification has the same meaning as is normally understood by a person of ordinary skill in the art to which the present invention pertains. The term as defined in commonly used dictionaries should be construed as having the same meaning in context as that in the related art and, unless otherwise explicitly defined in the present specification, should not be construed as having an excessively implied meaning or a purely literal meaning.

Exemplary embodiments of the present invention will be described in detail below with reference to the accompanying drawings. The same reference character refers to the same constituent element throughout the drawings.

In the case of dermis self-regeneration, a gas such as carbon dioxide is first injected to separate epidermal and dermal layers and to form a space. A skin regeneration accelerator such as hyaluronic acid is then injected into this space to promote dermis regeneration. In this manner, a retracted scar, a wrinkle, or the like is cured. However, for this dermis self-regeneration, it is necessary to inject two different gases repeatedly and/or alternately. To this end, two syringes may be used to inject two different gases. The inconvenience of this method is that the two syringes must be used alternately. The present invention was devised to avoid the alternating use of the two syringes.

FIG. 2 is a perspective view illustrating an injection unit 100 of a syringe for dermis regeneration according to an embodiment of the present invention. FIG. 3 is a perspective view illustrating the syringe for dermis regeneration according to the embodiment of the present invention. FIG. 4 is a view illustrating a state where a needle of the syringe for dermis regeneration according to the embodiment of the present invention enters skin.

With reference to FIGS. 2 to 4, the syringe for dermis regeneration according to the embodiment of the present invention includes the injection unit 100, a needle 200, a liquid supply unit 400, and a gas injection port 300. The injection unit 100 has a first space (not illustrated) therein and is open at a rear end portion thereof. The first space (not illustrated) is filled with a liquid or a gas and communicates with the outside. The needle 200 is combined with a front end portion of the injection unit 100 and has a space therein. The space communicates with the first space (not illustrated). The liquid supply unit 400 has a first end portion removably combined with the rear end portion of the injection unit 100, has a second end portion through which a piston 410 moves backward or forward, and has a space therein. The space is filled with the liquid and communicates with the first space (not illustrated). The piston 410 is inserted into the liquid supply unit 400. The gas injection port 300 passes through a sidewall of the injection unit 100 and communicates with the first space (not illustrated). The first space (not illustrated) is filled with the gas introduced through the gas injection port 300.

The injection unit 100 in the shape of a cylinder has a space therein. The injection unit 100 has the first space (not illustrated) therein. The first space (not illustrated) is filled with a liquid or a gas. The first space (not illustrated) is filled with the liquid supplied from the liquid supply unit 400 or the gas introduced through the gas injection port 300. When the piston 410 in the liquid supply unit 400 moves forward, the liquid or the gas within the first space (not illustrated) is discharged through the needle 200. The first space is illustrated in FIGS. 5 and 6 and a description thereof will be described.

The needle 200 has a space therein. The needle 200 is combined with the front end portion of the injection unit 100 in such a manner that the space within the needle 200 communicates with the first space (not illustrated). That is, a rear end portion of the needle 200 is inserted into the injection unit 100 and communicates with the first space (not illustrated).

The liquid supply unit 400 to which the needle 200 is not attached is a type of syringe. The liquid supply unit 400 has an opening at the first end portion and the space therewithin communicates with the first space (not illustrated) through the opening that the injection unit 100 has at the rear end portion. The piston 410 is inserted into the liquid supply unit 400 through the second end portion thereof.

The liquid supply unit 400 is separably combined with the rear end portion of the injection unit 100. For example, as illustrated, a flange 110 a portion of whose sidewall protrudes in a circumferential direction (in an outward direction) is provided on the rear end portion of the injection unit 100. The liquid supply unit 400 has a threaded combination portion at the first end portion. Accordingly, for combination, the flange 110 provided on the rear end portion of the injection unit 100 is screwed into the threaded combination portion provided on the rear end portion of the liquid supply unit 400.

The gas injection port 300 is provided to pass through the sidewall of the injection unit 100. Through the gas injection port 300, the first space (not illustrated) communicates with the outside. The first space (not illustrated) is filled with the gas introduced through the gas injection port 300. Through the gas injection port 300, the gas may be supplied from a cylinder 500 or the like that will be described below. To supply the gas, a separate gas injection apparatus may be connected to the gas injection port 300.

Accordingly, with the syringe for dermis regeneration according to the present invention, when supplying the gas, the liquid is prevented from remaining within the first space (not illustrated) communicating directly with the needle 200. Thus, when injecting the gas, the liquid is prevented from being first injected through the needle 200. In this manner, with the syringe for dermis regeneration, which is capable of alternately injecting the liquid and the gas, it is possible that an amount of the liquid and an amount of the gas can be appropriately adjusted independently of each other.

Particularly, the gas injection port 300 passes through the sidewall of the injection unit 100 in a manner that is adjacent to the rear end portion of the needle 200 positioned in front of the first space (not illustrated), and communicates with the first space (not illustrated). That is, the gas injection port 300 is provided in a manner that is adjacent to the rear end portion of the needle 200. For example, the gas injection port 300 is provided in such a manner that the central axis thereof is orthogonal to the rear end portion of the needle 200.

Accordingly, the gas introduced through the gas injection port 300 is supplied adjacent to the rear end portion of the needle 200. A phenomenon where the remaining liquid is discharged earlier than the gas through the needle 200 can be prevented as much as possible when injecting the gas.

In a state where the liquid supply unit 400 and the injection unit 100 are combined with each other, when the piston 410 moves forward, the liquid within the liquid supply unit 400 is discharged into the needle 200 through the first space (not illustrated). When the piston 410 moves backward, a negative pressure is formed in the first space (not illustrated), and thus the gas is introduced into the first space (not illustrated) through the gas injection port 300.

That is, when the piston 410 moves backward, the negative pressure is formed in the first space (not illustrated). Accordingly, the gas is introduced into the first space (not illustrated) through the gas injection port 300, and the first space (not illustrated) is filled with the gas. In a state where the first space (not illustrated) is filled with the gas, when the piston 410 moves forward, the gas within the first space (not illustrated) is first discharged through the needle 200, and the first space (not illustrated) is filled with the liquid within the liquid supply unit 400. When the piston 410 moves further forward, the liquid with which the first space (not illustrated) is filled is discharged through the needle 200.

Therefore, as the piston 410 moves backward, the first space (not illustrated) is filled with the gas. As the piston 410 moves forward, through the needle 200, the gas is first injected and then the liquid is sequentially injected. With the forward and backward movements of only one piston 410, the gas and the liquid can be sequentially injected.

A check valve 310 is provided in the gas injection port 300. The gas is injected into the first space (not illustrated) through the gas injection port 300. However, the liquid or the gas within the first space (not illustrated) does not flow to the outside through the gas injection port 300.

The check valve 310 allows a fluid to flow only in one direction and blocks the fluid from flowing in the opposite direction. The check valve 310 provided in the gas injection port 300 allows an external gas to flow into the first space (not illustrated) and blocks the liquid or the gas within the first space from flowing to the outside.

Accordingly, when the piston 410 moves backward, the gas is introduced into the first space (not illustrated) through the gas injection port 300. Conversely, when the piston 410 moves forward, the liquid or the gas within the first space (not illustrated) can be discharged through the needle 200 without flowing to the outside through the gas injection port 300.

The injection unit 100 has inclination surfaces 130 on portions of the sidewall. The portions are positioned at locations that do not overlap the Gas Injection Port 100. The inclination portions 130 are inclined toward the centerline of the injection unit 100 in a forward direction. The inclination surfaces 130 may be inclined inward in the forward direction The injection unit 100 may be cylinder-shaped. The injection unit 100 may have the inclination surfaces 130 that are formed by cutting opposite sides of a front surface of the injection unit in outward directions. Specifically, the injection unit 100 may have the inclination surfaces 130 that are formed by cutting portions that is outward from a straight line connecting two point on a circumferential edge of the injection unit 100.

With reference to FIG. 4, in the case of the syringe for dermis regeneration, in order to effectively inject a drug solution, the needle 200 has to enter skin at an angle of 45 degrees or less, not perpendicularly, with respect to the skin.

That is, as illustrated, an angle θ between the skin and the needle 200 is 45 degrees or less. To this end, as described above, the injection unit 100 has the inclination surfaces 130 on portions of the sidewall. The inclination angle θ between a direction of a straight line parallel to the center line of the injection unit 100 and each of the inclination surfaces 130 is 45 degrees or less.

Accordingly, when the needle 200 obliquely enters the skin, one of the inclination surfaces 130 is brought into contact with an upper surface of the skin for support. The skin does not cause interference with the injection unit 100. The needle 200 with a relatively short length can enter the skin to a sufficient depth.

The injection unit 100 has the inclination surfaces 130 on the sidewall at locations that do not overlap the gas injection port 300. Specifically, the injection unit 100 may have the inclination surfaces 130 on opposite sides of the sidewall. The inclination surfaces 130 have the form of facing each other.

Particularly, the injection unit 100 has the inclination surfaces 130 that are symmetrical in a direction perpendicular to opposite sides of the gas injection port 300. That is, the injection unit 100 has two inclination surfaces 130, facing each other in the direction perpendicular to opposite sides of the gas injection port 300, on the sidewall.

The gas injection port 300 is positioned between the inclination surfaces 130 on opposite sides facing each other. Particularly, the gas injection port 300 is positioned midway between the inclination surfaces 130 in opposite directions and is positioned as long a distance away from the inclination surfaces 130 in opposite directions as possible.

Accordingly, the inclination surfaces 130 are formed in such a manner that a separate component such as the check valve 310 is installed therein or that the gas injection port 300 connected to an external gas injection apparatus is positioned as far as therefrom as possible. In addition, it is possible that a position of the gas injection port can be changed in an upward-downward direction according to a direction of an external gas injection apparatus connected to the gas injection port 300. In the changed state of the position thereof, the needle 200 can enter the skin.

The needle 200 has a cut surface 210 that is formed by obliquely cutting the front end portion in one direction. Specifically, the cut surface 210 is formed by obliquely cutting the front end portion entering the skin in such a manner that the needle 200 easily enters the skin. That is, the front end portion of the needle 200 is obliquely cut and thus is much sharpened. Thus, the needle 200 easily enters the skin and has a wide opening in the obliquely cut surface 210. The liquid or the gas within the first space (not illustrated) is easily discharged.

Particularly, the cut surface 210 is formed by obliquely cutting the front end portion of the needle 200 in a direction parallel with the inclination surface 130 of the injection unit 100. That is, the cut surface 210 of the front end portion of the needle 200 is inclined in parallel with the inclination surfaces 130 of the injection unit 100.

The two inclination surfaces 130, in opposite directions, of the injection unit 100 are present as described above. The cut surface 210 may be formed by obliquely cutting the front end portion of the needle 200 in a direction parallel with one of the two inclination surfaces 130.

It is preferable that the cut surface 210 of the front end portion of the needle 200 faces toward an upper portion of the skin in a state where the cut surface 210 remains in the skin. The reason for this positioning of the cut surface 210 is that the injection of the liquid or the gas into an upper portion of the dermis through the front end portion of the needle 200 entering between epidermis and dermis is effective in the dermis regeneration. Accordingly, the liquid or the gas within the first space (not illustrated) is injected in a state where the cut surface 210, in parallel with the inclination surface 130, of the front end portion of the needle 200 faces toward the upper portion of the skin.

FIG. 5 is a perspective view illustrating a syringe for dermis regeneration according to another embodiment of the present invention. FIGS. 6 and 7 are cross-sectional views illustrating a syringe for dermis regeneration according to still another embodiment of the present invention.

The syringe for dermis regeneration according to the embodiment of the present invention further includes a cylinder 500. The cylinder 500 has a double-tube structure that includes an inner tube 510 and an outer tube 520 that are combined with a rear end portion of the injection unit 100. The inner tube 510 has a second space 530 therein. A third space 540 is formed between the inner tube 510 and the outer tube 520. The liquid supply unit 400 communicating with the first space 120 is positioned within the second space 530. The third space 540 communicates with the first space 120 through the gas injection port 300 and is filled with the gas.

That is, the cylinder 500 having the double-tube structure is combined with a rear end portion of the injection unit 100. The liquid supply unit 400 is positioned in the second space 530 within the inner tube 510 of the cylinder 500. The third space 540 between the inner tube 510 and the outer tube 520 is filled with the gas. The gas is supplied to the first space 120 through a gas supply unit.

Accordingly, only the liquid supply unit 400 that is a type of separable syringe is inserted into and separated from the second space 530. Thus, with the syringe for dermis regeneration having the double-tube structure, the liquid and the gas can be sequentially discharged.

The sidewall of the injection unit 100 has a combination end portion 140 that is recessed inward. The cylinder 500 is combined with the combination end portion 140 in such a manner that the second space 530 is sealed by the combination end portion 140.

Particularly, as illustrated in FIG. 6, the combination end portion 140 in a direction parallel with the gas injection port 300 may be surrounded by the outer tube 520 and the inner tube 510 and may seal the second space 530.

In addition, as illustrated in FIG. 7, a combination end portion 140' in the direction adjacent to the inclination surface 130 may be surrounded by front walls of the inner tube 510 and the outer tube 520 and thus may seal the second space 530.

Additionally, a guidance portion 550 is provided on a sidewall of the outer tube 520 of the cylinder 500 in the direction adjacent to the inclination surface 130 of the injection unit 100. The guidance portion 550 includes a plurality of grooves and a plurality of protrusions that are positioned in an alternating manner. The guidance portion 550 is provided to guide a position of an actuator (not illustrated) that drives the piston 410 inserted into the liquid supply unit 400 or guides a connection line connected to the actuator (not illustrated).

Particularly, the guidance portion 550 is provided on the sidewall of the outer tube 520 of the cylinder 500 in the direction adjacent to the inclination surface 130 in such a manner that the guidance portion 550 is positioned as long a distance away from the skin as possible. Thus, the guidance portion 550 is vertically positioned as long a distance away from the skin as possible when the needle 200 enters the skin.

A syringe for dermis regeneration according to another embodiment of the present invention includes an injection unit 100, a cylinder 500, a needle 200, a liquid supply unit 400, and a gas injection port 300. The injection unit 100 has a first space 120 therein and is open at a rear end portion thereof. The first space 120 is filled with a liquid or a gas and communicates with the outside through the open rear end portion. The cylinder 500 has a double-tube structure that includes an inner tube 510 and an outer tube 520 that are integrally combined with a rear end portion of the injection unit 100. The inner tube 510 has a second space 530 therein. A third space 540 is formed between the inner tube 510 and the outer tube 520. The needle 200 is combined with a front end portion of the injection unit 100 and has a space therein. The space communicates with the first space 120. The liquid supply unit 400 is inserted into the second space 530. The liquid supply unit 400 has a first end portion removably combined with the rear end portion of the injection unit 100, has a second end portion through which a piston 410 moves backward or forward, and has a space therein. The space is filled with the liquid and communicates with the first space 120. The piston 410 is inserted into the liquid supply unit 400. The gas injection port 300 passes through a sidewall of the injection unit 100 and communicates with the first space 120 and the third space 540. The first space 120 is filled with the gas introduced from the third space 540 through the gas injection port 300.

That is, according to another embodiment, the injection unit 100 and the cylinder 500 are integrally combined with each other, without employing the structure in which the injection unit 100 and the cylinder 500 are separately provided and combined with each other. Accordingly, with this relatively simple configuration, an amount of injected gas and an amount of injected liquid can be adjusted independently of each other and can be sequentially discharged.

With the syringe for dermis regeneration according to the present invention, a gas such as carbon dioxide and a drug solution such as hyaluronic acid can be selectively injected and the dermis, which is an inner layer of the skin, can be easily regenerated. Furthermore, the relatively simple configuration makes it fairly easy to distribute and use the syringe for dermis regeneration.

The exemplary embodiments of the present invention are illustrated and described, and it would be obvious to a person of ordinary skill in the art that various modifications and alterations are possibly made to the present invention without departing from the technical idea of the present invention that is claimed in the following claims.

DESCRIPTION OF THE REFERENCE NUMERALS IN THE DRAWINGS

| 100: Injection Unit, | 200: Needle |
|---|---|
| 300: Gas Injection Port, | 400: Liquid Supply Unit |
| 500: Cylinder | |

The invention claimed is:

1. A syringe for dermis regeneration, the syringe comprising:

an injection unit having a first space therein and being open at a rear end portion thereof, the first space being filled with a liquid or a gas and communicating with the outside through the open rear end portion;

a needle combined with a front end portion of the injection unit and having a space therein, the space of the needle communicating with the first space;

a liquid supply unit having a first end portion removably combined with the rear end portion of the injection unit, having a second end portion through which a piston moves backward or forward, and having a space therein, the space of the liquid supply unit being filled with the liquid and communicating with the first space, and the piston being inserted into the liquid supply unit through the second end portion of the liquid supply unit;

a gas injection port passing through a sidewall of the injection unit and communicating with the first space to allow the first space to be filled with the gas introduced through the gas injection port; and a cylinder having a double-tube structure that comprises an inner tube and an outer tube that are connected to a rear end portion of the injection unit, the inner tube having a second space therein and a third space being formed between the inner tube and the outer tube, wherein the liquid supply unit communicating with the first space is positioned within the second space, and the third space communicates with the first space through the gas injection port and is filled with the gas.

2. The syringe of claim 1 wherein the gas injection port passes through the sidewall of the injection unit in a manner that is adjacent to a rear end portion of a needle positioned in front of the first space and communicates with the first space.

3. The syringe of claim 1, wherein, in a state where the liquid supply unit is combined with the injection unit, when the piston moves forward, the liquid within the liquid supply unit is discharged into the needle through the first space, and when the piston moves backward, a negative pressure is formed in the first space, and thus the gas is introduced into the first space through the gas injection port.

4. The syringe of claim 1, wherein a check valve is provided in the gas injection port, and the gas is injected into the first space through the gas injection port, but the liquid or the gas within the first space does not flow to the outside through the gas injection port.

5. The syringe of claim 1, wherein the injection unit has an inclination surface on a portion of the sidewall, the portion being positioned at a location that does not overlap the gas injection port, and the inclination portion being inclined toward a centerline of the injection unit in a forward direction.

6. The syringe of claim 5, wherein the inclination surface of the injection unit comprises inclination surfaces formed on opposite sides of the sidewall, the inclination surfaces having a form of facing each other.

7. The syringe of claim 6, wherein the gas injection port is positioned on the sidewall of the injection unit at a location between the opposite inclination surfaces facing each other.

8. The syringe of claim 5, wherein the needle has a cut surface that is formed by obliquely cutting a front end portion of the needle in a direction parallel with the inclination surface of the injection unit.

9. The syringe of claim 1, wherein the injection unit is cylinder-shaped and has inclination surfaces formed by cutting opposite sides of a front surface of the injection unit in outward directions.

10. The syringe of claim 1, wherein the needle has a cut surface that is formed by obliquely cutting a front end portion of the needle in one direction.

11. The syringe of claim 1, wherein a sidewall of the injection unit has a combination end portion recessed inward and the cylinder is combined with the combination end portion in such a manner that the second space is sealed by the combination end portion.

12. The syringe of claim 1, wherein the injection unit has inclination surfaces on portions of a sidewall thereof, the portions being positioned at locations that do not overlap the gas injection port, and the inclination portions being inclined toward a centerline of the injection unit in a forward direction, and the outer tube of the cylinder in a direction adjacent to the inclination surfaces of the injection unit has a guidance portion on a sidewall thereof, the guidance portion comprising a plurality of grooves and a plurality of protrusions that are positioned in an alternating manner.

13. A syringe for dermis regeneration, the syringe comprising:

an injection unit having a first space therein and being open at a rear end portion thereof, the first space being filled with a liquid or a gas and communicating with the outside through the open rear end portion;

a cylinder having a double-tube structure that comprises an inner tube and an outer tube that are integrally combined with a rear end portion of the injection unit, the inner tube having a second space therein and a third space being formed between the inner tube and the outer tube;

a needle combined with a front end portion of the injection unit and having a space therein, the space of the needle communicating with the first space;

a liquid supply unit having a first end portion removably combined with the rear end portion of the injection unit, having a second end portion through which a piston moves backward or forward, and having a space therein, the space of the liquid supply unit being filled with the liquid and communicating with the first space, and the piston being inserted into the liquid supply unit through the second end portion of the liquid supply unit; and a gas injection port passing through a sidewall of the injection unit and communicating with the first space and the third space, the first space being filled with the gas introduced from the third space through the gas injection port.

* * * * *